(12) United States Patent
Klint

(10) Patent No.: US 6,383,146 B1
(45) Date of Patent: May 7, 2002

(54) GUIDEWIRE

(75) Inventor: Henrik Sønderskov Klint, Lyngby (DK)

(73) Assignees: Cook Incorporated, Bloomington, IN (US); William Cook Europe ApS (DK)

( * ) Notice: Subject to any disclaimer, the term of this patent is extended or adjusted under 35 U.S.C. 154(b) by 0 days.

(21) Appl. No.: 09/538,066

(22) Filed: Mar. 29, 2000

(30) Foreign Application Priority Data

Mar. 29, 1999 (EP) .............................................. 99610023

(51) Int. Cl.$^7$ ................................................. A61B 5/00
(52) U.S. Cl. ........................................ 600/585; 604/523
(58) Field of Search ................................. 600/433, 434, 600/435, 585; 604/523, 531

(56) References Cited

U.S. PATENT DOCUMENTS

| | | |
|---|---|---|
| 4,003,369 A | 1/1977 | Heilman et al. |
| 4,548,206 A | 10/1985 | Osborne |
| 4,619,274 A | 10/1986 | Morrison |
| 4,917,102 A | 4/1990 | Miller et al. |
| 4,932,419 A | 6/1990 | de Toledo |
| 4,934,380 A | 6/1990 | de Toledo |
| 4,994,069 A | 2/1991 | Ritchart et al. |
| 5,001,825 A | 3/1991 | Halpern |
| 5,069,217 A | 12/1991 | Fleischhacker, Jr. |
| 5,108,407 A | 4/1992 | Geremia et al. |
| 5,122,136 A | 6/1992 | Guglielmi et al. |
| 5,131,406 A | 7/1992 | Kaltenbach |
| 5,171,383 A | 12/1992 | Sagaye et al. |
| 5,178,158 A | 1/1993 | de Toledo |
| 5,184,621 A | 2/1993 | Vogel et al. |

(List continued on next page.)

FOREIGN PATENT DOCUMENTS

| | | |
|---|---|---|
| DE | 3641935 | 6/1987 |
| DE | 19829620 | 2/1999 |
| EP | 0119688 | 9/1984 |
| EP | 0318046 | 5/1989 |
| EP | 0369383 | 5/1990 |
| EP | 9304722 | 3/1993 |
| EP | 0820782 | 1/1998 |
| EP | 0826389 | 3/1998 |
| EP | 0680351 | 8/1998 |
| WO | 9113592 | 9/1991 |
| WO | 9213483 | 8/1992 |
| WO | 9219151 | 11/1992 |
| WO | 9305842 | 4/1993 |
| WO | 9306883 | 4/1993 |
| WO | 9311823 | 6/1993 |
| WO | 9406502 | 3/1994 |
| WO | 9406503 | 3/1994 |
| WO | 9407560 | 4/1994 |
| WO | 9409705 | 5/1994 |
| WO | 9816274 | 4/1998 |

OTHER PUBLICATIONS

Written Opinion issued Jan. 11, 2000 on corresponding PCT application.

Written Opinion issued Dec. 13, 2001 on Application No. PCT/US00/08543.

*Primary Examiner*—Kevin Shaver
*Assistant Examiner*—Pamela S Wingood
(74) *Attorney, Agent, or Firm*—Richard J. Godlewski

(57) ABSTRACT

A guidewire comprising a distal end (2), a shaft portion (4) and a proximal end (3), wherein the shaft portion comprises a single helically wound, ribbon-shaped wire (7) having a pitch angle ($\alpha$) in the range of 35° to 76°, and said helical wound wire preferably has a smaller total outer diameter at the distal end than at its proximal end.

15 Claims, 3 Drawing Sheets

U.S. PATENT DOCUMENTS

| | | |
|---|---|---|
| 5,184,627 A | 2/1993 | de Toledo |
| 5,217,484 A | 6/1993 | Marks |
| 5,234,003 A | 8/1993 | Hall |
| 5,234,437 A | 8/1993 | Sepetka |
| 5,238,004 A | 8/1993 | Sahatjian et al. |
| 5,243,996 A | 9/1993 | Hall |
| 5,250,071 A | 10/1993 | Palermo |
| 5,373,619 A | 12/1994 | Fleischhacker et al. |
| 5,376,083 A | 12/1994 | Mische |
| 5,411,476 A | 5/1995 | Abrams et al. |
| 5,419,339 A | 5/1995 | Palmer |
| 5,488,959 A | 2/1996 | Ales |
| 5,546,948 A | 8/1996 | Hamm et al. |
| 5,643,278 A | 7/1997 | Wijay |
| 5,645,064 A | 7/1997 | Littmann et al. |
| 5,690,666 A | 11/1997 | Berenstein et al. |
| 5,695,483 A | 12/1997 | Samson |
| 5,720,300 A | 2/1998 | Fagan et al. |
| 5,725,534 A | 3/1998 | Rasmussen |
| 5,759,161 A | 6/1998 | Ogawa et al. |
| 5,800,455 A | 9/1998 | Palermo et al. |
| 5,957,940 A | 9/1999 | Tanner et al. |
| 5,984,877 A | 11/1999 | Fleischhacker, Jr. |

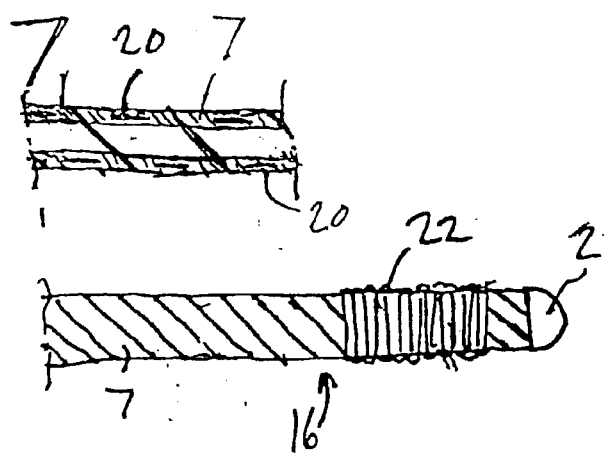
Fig. 3
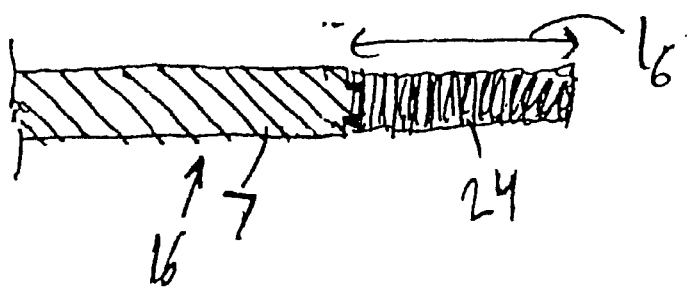
Fig. 4
Fig. 5
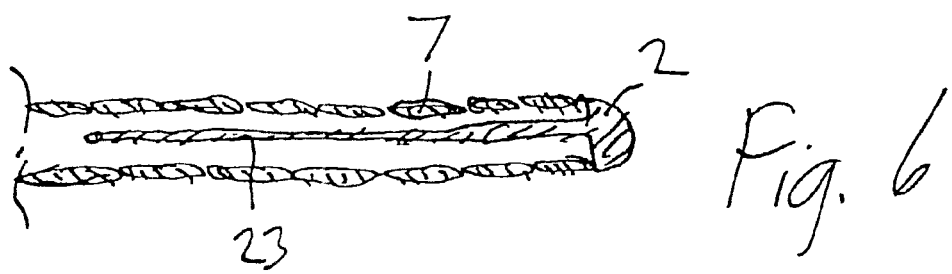
Fig. 6

GUIDEWIRE

CROSS-REFERENCE TO RELATED APPLICATIONS

This application claims priority of European Patent Application No. 99610023.6 filed Mar. 29, 1999 in the European Patent Office.

TECHNICAL FIELD

The present invention relates to medical devices and more particularly to a guidewire for vascular procedures.

BACKGROUND OF THE INVENTION

Medical guidewires for vascular procedures, such as angioplasty procedures, diagnostic and interventional procedures, percutaneous access procedures, or radiological and neuroradiological procedures in general, traditionally comprise an elongated core element with one or more tapered sections near the distal end thereof and a flexible helical coil disposed about the distal portion of the core element. The distal extremity of the core element or a separate safety ribbon which is secured to the distal extremity of the core element extends through the flexible coil and is secured to the distal end member of the guidewire, which is a rounded member at the distal end of the helical coil. Torquing means are provided on the proximal end of the core element to rotate and steer the guidewire while it is being advanced through a patient's vascular system.

The physician views the progress on a screen and causes the distal end of the guidewire to enter and follow tortuous vascular vessels from the entry site through the various vascular branches to the target site, by pushing and rotating the proximal end of the guidewire outside of the patient. In connection with the advancement of the guidewire once the guidewire has been positioned at the desired site, a wide variety of medical devices may be directed to the target site along the guidewire by simply sliding the device over the guidewire and advance the device to the distal end of the guidewire. A typical medical device is a catheter; very often a catheter and the guidewire are introduced in a common procedure where the guidewire is advanced a distance in front of the catheter, then the catheter is advanced over the guidewire, followed by a further advancement of the guidewire, and so forth. Following placement of the catheter or other device, the guidewire can be removed if desired.

The flexible coil acts as a protective measure of a suitably large diameter, hindering the guidewire core in damaging the vascular wall. The above mentioned guidewire is known from U.S. Pat. No. 4,619,274 to Morrison whose guidewire has a progressively attenuated diameter. An elongated core element extends from the proximal to the distal ends of the guidewire and has a decreasing cross sectional area in a direction towards the distal end member. A coil is carried by and secured to said core element and has proximal and distal ends. The coil has a diameter which decreases in a direction towards the distal end. The coil is formed of a single helical wound wire which has a diameter which decreases from one end to the other end with the larger diameter beginning in a region closer to the proximal end and the smaller diameter wire ending in a region closer to the distal end.

U.S. Pat. No. 5,001,825 to Halpern describes a fabrication process for a guidewire core where a solid metal wire is drawn down in several stages to have a stepwise decreasing diameter towards the distal end. The core is surrounded by a flexible coil having an outer diameter which decreases near the distal end. The coil consists of a single helical wound wire having a constant cross sectional area. The core element transfers the torque to the distal area of the guidewire, but the core element also restricts the flexibility of the guidewire. When the core element is given a very small diameter in its distal area in order to improve the flexibility, it loses the ability to transfer the torque.

It is an object of the present invention to provide a guidewire which in its distal area is highly flexible and yet capable of transferring torques applied to the proximal end of the guidewire to the distal end of the guidewire in a very precise manner even when the guidewire follows a loop-shaped course.

SUMMARY OF THE INVENTION

In view of this, the guidewire according to the present invention comprises a distal end member and a shaft portion extending in a longitudinal direction from a proximal end towards the distal end member, and a single helical wound wire extending from a position at the shaft portion to the distal end member. The inventive guidewire is characterized in that the single helical wound wire is ribbon-shaped and has a pitch angle in the range of 35°–76°.

When, according to the invention, the flexible coil in the distal end of the guidewire is ribbon-shaped and wound with a pitch angle in the specified range, the wound wire transfers torque, and also force components directed in the axial direction of the guidewire, to the distal end thereof. The guidewire surprisingly maintains its capabilities for transferring torque when it follows a tortuous path involving two or more loops. The torque is transferred all the way to the distal end member or tip of the guidewire, meaning that the distal end member can be very precisely steered from the proximal end. The widest cross sectional dimension, the breadth, of the ribbon-shaped wire is directed in the longitudinal direction of the guidewire. It is preferred that the ribbon-shaped wire has rounded edges.

In a preferred embodiment, along a distance of at least 10 cm from the distal end member said ribbon-shaped wire is the primary or the sole torque-transferring means between the shaft portion and the distal end member. Because the torque is transferred through the ribbon-shaped wire the central core can be given very feeble dimensions, thus increasing the flexibility of the distal portion, or it can be completely left out by making at least the most distal 10 cm of the guidewire without a torque-transferring solid metallic core inside said ribbon-shaped wire. If desired there can be a safety ribbon inside the ribbon-shaped wire, connecting the rounded distal end member with a more proximal shaft portion, but such a safety ribbon will normally not be required.

Due to the very high flexibility, pushability and torquability and the ability of the guidewire to maintain each of these three characteristics even when set in a very tortuous pattern involving two or more tight loops the guidewire can be of use in very small and distant vessels. In order to further enhance use of the guidewire in vessels with small lumen the ribbonshaped wire can have a smaller outer diameter at the distal end than at said position on the shaft portion.

If the ribbon-shaped wire is secured to the shaft, which can, for example, be of traditional type with a core member or can be another ribbon-shaped wire of larger dimensions, such as by soldering or welding the proximal end of the wire onto the shaft the guidewire can be prone to kinking at the transition between the wire and the remainder of the shaft. With a view to avoiding this, the helical wound wire preferably extends into the shaft portion towards the proximal end, and even more preferably it extends along a guidewire length at least in the range of 20–50 cm from the distal end. The additional stiffness caused by the attachment of the wire is less disturbing the farther it occurs from the distal end of the guidewire. It is possible to let the ribbon-shaped wire extend to a position at the proximal end of the guidewire, so that is spans the entire guidewire.

In the preferred embodiment the guidewire is made without a solid or hollow metallic core inside the at least one coil. By dispensing with the metallic core the flexibility of the guidewire is increased, and the manufacturing of the guidewire is simplified.

In an embodiment the radial thickness of the ribbon-shaped wire is larger in the proximal portion of the guidewire than in the distal portion thereof. Such a variation of the cross-sectional shape can be the result of grinding of a helical wound wire on its outside with the purpose of reducing the diameter of the helical wound wire in its distal portion. The reduced cross-sectional area greatly increases the bending flexibility of the helical wound wire without sacrificing its ability to transfer torque.

The present invention also relates to a method of manufacturing a guidewire, wherein a guidewire body is provided, said body comprising at single helical wound, ribbon-shaped wire having a pitch angle in the range of 35°–76°, wherein an elongate distal guidewire portion of said guidewire body is subjected to grinding reducing the outer diameter of said distal guidewire portion in relation to a proximal portion of the guidewire. Grinding is an advantageous manner of manufacturing the above mentioned guidewires because it is very easy to adapt the grinding process to the specific guidewire to be produced, and a wide variety of guidewires can be pre-manufactured as wound guidewire bodies having an even outer diameter along their entire length. When the specific use of the guidewire is specified, such as a guidewire for accessing a kidney in an adult via the femoral route, which requires a guidewire having a relatively long portion with the full diameter and a relatively short portion with a quickly reduced diameter, or a guidewire for neuroradiological use via the femoral route, which requires a gentle reduction in diameter over a relatively long distance and a long and soft distal portion, it is a simple matter to adjust the grinding process to the desired guidewire.

The method can be adjusted to grind the elongate distal portion of the guide wire to have a substantially continuously diminishing outer diameter which results in a gradual increase of bending flexibility of the guidewire. It is further possible to adjust the method to grind the elongate distal portion of the guide wire to have a substantially stepwise diminishing outer diameter which is often preferable in case of very long distal portions.

Further, the method can be so that elongate distal portions of the guide wire are ground to have areas with diminishing outer diameters mixed with areas having substantially constant outer diameters.

BRIEF DESCRIPTION OF THE DRAWINGS

Examples of the invention will now be described in more detail with reference to the highly schematical drawings, in which:

FIGS. 3–6 depict partial, longitudinal sections through helical wound wires in embodiments of the guidewire with a radiopaque marker in the distal end.

DETAILED DESCRIPTION

Figure 1:
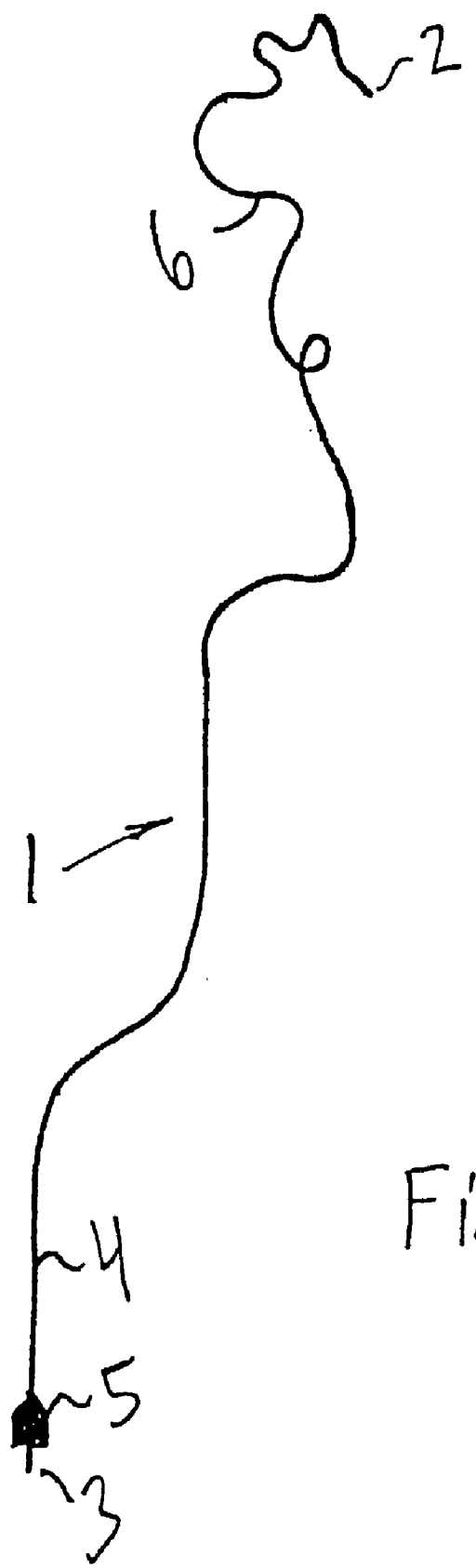
FIG. 1 depicts a sketch of a guidewire according to the invention when following an example of a course in the vascular system.

In the following description of the embodiments, the same reference numerals are used for features of the same type. A guidewire seen in FIG. 1 is generally denoted by 1 and has a distal end 2 capable of being advanced to a target site in the vascular system and a proximal end 3 that is kept outside the patient's body. A shaft portion 4 extends from the proximal end towards the distal end and carries near the proximal end a handle 5 releasably secured to the guidewire. The guidewire can typically have a length in the range of 50–300 cm and a maximum outer diameter in the range of 0.204–1.072 mm (0.008–0.042 inches). It can also include several segments where the proximal segment has a larger diameter than one or more intermediate segments which has/have larger diameter(s) than the distal segment. When such a guidewire follows a tortuous vessel path involving several sharp bends, loops and so forth, it is desirable that a turning of handle 5 results in a similar turning of the distal end 2.

The shaft portion 4 can include a solid shaft which is of a metallic material such as medical grade stainless steel or Nitinol. In that case a coiled distal portion 6 is fixed onto and in extension of the shaft portion. However, in the preferred embodiment the coiled portion continues from the distal end to the proximal end, and the use of a solid shaft is made superfluous.

The coiled portion ends distally at the distal end member 2, which is a member having a soft front end termination, such as a rounded front or a front of very flexible material or very flexible configuration. End member 2 can be a drop of solder, or a sphere that can be, for example, laser welded onto the distal end of the coiled portion. Further, end member 2 can also include a soft coil of radiopaque material.

Figure 2:
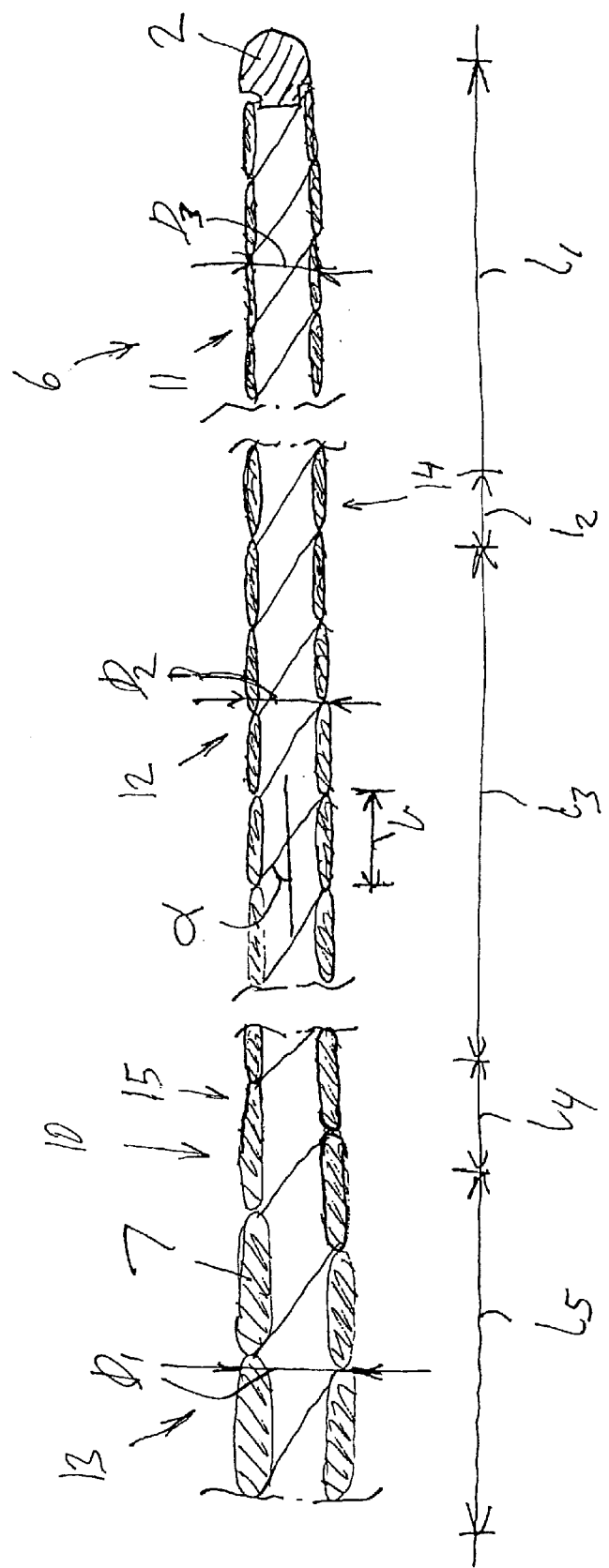
FIG. 2 illustrates a partial, longitudinal section 25 through an embodiment of the guidewire.

In the embodiment depicted in FIG. 2 a single ribbon-shaped wire 7 has been wound with the windings in mutual abutment and with a pitch angle $\alpha$ of the individual wire of about 40°. The pitch angle is the included angle between the longitudinal axis of the guidewire and the center axis of the wire 7. The size of the pitch angle depends on the breadth of the wire and of the diameter of the guidewire. If the pitch angle is smaller than 35° the guidewire becomes prone to kinking, and if the pitch angle becomes larger than 76° the desired torquability is not obtained. A pitch angle of 74° provides a guidewire with fine torquability. The most preferred pitch angle is in the range of 40 to 70°. A pitch angle in the range of 35–40° is also very useful and allows certain modifications to be made to the properties of the guidewire. If pushability is the most important criteria, the pitch angle can be chosen at, for example, 38°; and if the bending flexibility is most important the pitch angle can be chosen at 75°, for example. However, the combination of torque transferral, pushability and transverse flexibility is normally well-balanced for pitch angles in the range of 50–68°. The pitch or pitch distance is indicated by b and is largely the same as the breadth of the ribbon-shaped wire.

The wire 7 is of a linear elastic material, such as stainless steel, titanium or tantalum, or it is made of a superelastic alloy, such as Nitinol. The breadth of the wire can be in the range of 0.03–0.45 mm, and preferably in the range of 0.10–0.35 mm, and the thickness of the wire can be in the range of 0.02–0.23 mm, and preferably in the range of 0.04–0.16 mm. In case the wire is of stainless steel, it has preferably an ultimate tensile strength in the range of 1800–2700 N/mm$^2$ but lower or higher values are also possible. The guidewire is made by winding the ribbon-shaped wire about a mandrel. Then the mandrel with the coiled wire can be subjected to heat treatment in order to remove residual stresses from the wire. As an example, the heat treatment can last for about two hours in an oven at a temperature of about 500° C. After the heat treatment the mandrel is removed from the wires.

In the embodiment shown in FIG. 2 the distal portion 6 has a plurality of sections 11, 12 and 13 having sequentially smaller outer diameters D1, D2 and D3 towards distal end member 2 with tapered sections 14 and 15 connecting the smaller diameter sections with larger diameter sections. The sections with reduced diameter have been manufactured by grinding the distal portion in a centerless grinding machine. The inner diameter of the sections 11–13 is preferably constant.

In the ground portions, wire 7 has a smaller radial thickness. In the shaft portion the guidewire has a diameter D1 corresponding to the diameter of the coil prior to its grinding where the wire 7 has its full cross-sectional area. This diameter is present along the length 15.

The grinding procedure produces the tapered section 15 in which the outer diameter diminishes to diameter D2, and the tapered section 14 in which the outer diameter of the guidewire diminishes to diameter D3. Due to the smaller outer diameters, sections 13 and 11 have considerably larger transverse flexibility and higher softness, but torque is nevertheless surprisingly transferred fully to the distal end.

In order to make the tip portion of the guidewire more visible on a screen, it is desirable to use some kind of radiopaque material, such as platinum which in itself lacks the desirable high strength properties provided by the use of stainless steel, Nitinol or another material of high strength and large flexibility and elasticity. In the embodiment illustrated in FIG. 3 by a sectional view of the distal portion, a part 20 of the ribbon-shaped wire 7 is of the radiopaque material and the remaining part is of the high strength material. The part 20 can have a relatively short length.

As an alternative, a guidewire distal portion 16 of the type shown in FIG. 2 can be provided with a coil of radiopaque wire which has a very small wire diameter, such as 0.05–0.35 mm. The coil has a pitch distance corresponding to the diameter of the wire, and consequently coil 22 is unable to transfer torque and is very flexible so that the desired properties of the distal guidewire portion are not impaired by adding coil 22 to the guidewire. Another embodiment according to the invention is outlined in FIG. 6 where tip 2 is of radiopaque material and includes a thread or a ribbon 23 of similar material that extends centrally into the hollow inner space in the guidewire to a free end. Further, it is possible to position a distal tip member designed as a very soft coil 24 of radiopaque material in extension of wire 7 as outlined in FIG. 5. Such a coil can, for example, have a length 16 of about 35 mm. Apart from making the tip visible it can also serve as a very soft and pliable tip member.

The guidewire can be made with a uniform diameter throughout its length. In case the guidewire has diminishing diameter towards the distal end a prefabricated guidewire of uniform diameter can be ground to the desired dimensions as described above.

As an alternative or supplement to grinding, the guidewire can be composed of several wire portions in which the wires have mutually different diameters and cross-sectional areas. In a proximal portion the wires can have a larger diameter than the wires in one or more intermediate portions, and these can have larger diameter than the wires in a distal portion.

It is preferred that the ribbon-shaped wire has a breadth b which is from 2 to 6 times the thickness in the radial direction of the guidewire. As an example the breadth can be of about 0.24 mm and the thickness, of about 0.06 mm.

The various embodiments can be combined into other embodiments within the scope of the present invention. Other modifications are possible, such as using a core member within the coiled wires, which core member can extend along the proximal and any intermediate portions but not along the distal portion. The core member can have a cross-sectional area that diminishes gradually or stepwise at increasing distance from the proximal end of the guidewire.

What is claimed is:

1. A guidewire comprising a distal end member and a shaft portion extending in a longitudinal direction from a proximal end towards the distal end member, and a single helical wound wire extending from a position at the shaft portion to the distal end member, characterized in that the single helical wound wire is ribbon-shaped, and has windings that are in mutual abutment and have a pitch angle in the range of 35° to 74°.

2. A guidewire according to claim 1, characterized in that the pitch angle is in the range of 50° to 68°.

3. A guidewire according to claim 1, characterized in that along a distance of at least 10 cm from the distal end member said ribbon-shaped wire is the primary or the sole torque-transferring means between the shaft portion and the distal end member.

4. A guidewire according to claim 1, characterized in that at least in the most distal 10 cm of the guidewire is without a torque-transferring solid metallic core inside said ribbon-shaped wire.

5. A guidewire according to claim 1, characterized in that the ribbon-shaped wire has a smaller outer diameter at the distal end than at said position on the shaft portion.

6. A guidewire according to claim 1, characterized in that said ribbon-shaped wire has windings abutting other windings of itself along a guidewire length at least in the range of 20–50 cm from the distal end.

7. A guidewire according to claim 6, characterized in that said ribbon-shaped wire extends to a position at the proximal end of the guidewire.

8. A guidewire according to claim 7, characterized in that the guidewire is without a solid or hollow metallic core inside the ribbon-shaped wire.

9. A guidewire according to claim 8, characterized in that the radial thickness of the ribbon-shaped wire is larger in the proximal portion of the guidewire than in the distal portion.

10. A guidewire according to claim 1, characterized in that the guidewire is assembled of two or more segments having different outer diameters.

11. A guidewire according to claim 5, characterized in that the ribbon-shaped wire has a thickness adjacent the distal end that is less than its thickness remote from the distal end.

12. A guidewire according to claim 11, characterized in that outwardly facing portions of the guidewire have been ground away to reduce the outer diameter of the guidewire along the distal portion.

13. A guidewire according to claim 1, characterized in that edges of the ribbon-shaped wire are rounded.

14. A guidewire according to clam 1, characterized in that the windings have a pitch angle in the range of 35° to 70°.

15. A guidewire according to claim 1, characterized in that the windings have a pitch angle in the range of 40° to 70°.

* * * * *